United States Patent [19]

Richardson et al.

[11] Patent Number: 4,560,697
[45] Date of Patent: Dec. 24, 1985

[54] 1,3-BIS-(1H-1,2,4-TRIAZOL-1-YL)-2-PER-FLUORO-ALKYLPROPAN-2-OL ANTIFUNGAL AGENTS

[75] Inventors: Kenneth Richardson; Peter J. Whittle, both of Canterbury, England

[73] Assignee: Pfizer Inc., New York, N.Y.

[21] Appl. No.: 571,218

[22] Filed: Jan. 16, 1984

[30] Foreign Application Priority Data

Jan. 29, 1983 [GB] United Kingdom ............. 8302500

[51] Int. Cl.⁴ .................. A01N 43/64; A61K 31/41; C07D 249/08
[52] U.S. Cl. .................. 514/383; 260/456 R; 548/262; 568/842
[58] Field of Search ............ 548/262; 424/269; 514/383

[56] References Cited

U.S. PATENT DOCUMENTS 4,359,470 11/1982 Kramer et al. ............... 548/262
4,382,944 5/1983 Kramer et al. ............... 548/262
4,416,682 11/1983 Worthington ................. 71/76
4,428,949 1/1984 Kramer et al. ............... 548/262

OTHER PUBLICATIONS

Burger, Medicinal Chemistry, (Second Edition) (New York, 1960), p. 1055.

*Primary Examiner*—Alton D. Rollins
*Attorney, Agent, or Firm*—Charles J. Knuth; Albert E. Frost; Paul D. Thomas

[57] ABSTRACT

Compounds of the formula

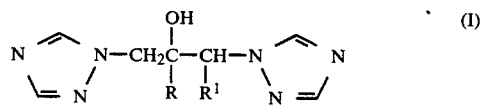

or a pharmaceutically or agriculturally acceptable acid addition salt thereof wherein R is ($C_1$–$C_5$) perfluoroalkyl and $R^1$ is H or $CH_3$, method for their use in combatting fungal infections in plants, seeds and animals, including humans; and as antileishmanial agents, and pharmaceutical and agricultural compositions containing them.

12 Claims, No Drawings

1,3-BIS-(1H-1,2,4-TRIAZOL-1-YL)-2-PERFLUORO-ALKYLPROPAN-2-OL ANTIFUNGAL AGENTS

BACKGROUND OF THE INVENTION

This invention relates to novel triazole derivatives which have antifungal activity and are useful in the treatment of fungal infections in animals, including humans, and as agricultural fungicides. They also have antileishmanial activity.

1,3-bis-(1H-1,2,4-triazol-1-yl)-2-substituted-propan-2-ol antifungal agents having an optionally substituted alkyl or phenyl group as a 2-substituent are disclosed in U.S. Pat. No. 4,416,682, issued Nov. 22, 1983 on an application filed June 2, 1981 and claiming the same priority as Great Britain Patent Application GB No. 2,078,719A. The 2-alkyl substituent includes $C_1$–$C_6$-haloalkyl but not perhaloalkyl.

SUMMARY OF THE INVENTION

According to the invention, there are provided compounds of the formula

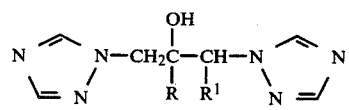

where R is a $C_1$–$C_5$ perfluoroalkyl group; and $R^1$ is H or $CH_3$; and their pharmaceutically and agriculturally acceptable acid addition salts.

When R contains 3, 4 or 5 carbon atoms, it can be straight or branched chain. R is preferably straight chain.

The invention also provides a pharmaceutical composition comprising an antifungal or antileishmanial amount of a compound of the formula (I) or a pharmaceutically acceptable acid addition salt thereof, together with a pharmaceutically acceptable diluent or carrier.

The invention further provides a compound of the formula (I) or a pharmaceutically acceptable acid addition salt thereof, for use in medicine, in particular for treating fungal infections in animals, including humans, or for treating leishmaniasis.

The invention also provides an agricultural (including horticultural) antifungal composition suitable for use on a plant or seed which comprises an antifungal amount of a compound or agriculturally acceptable salt of formula (I) and an agriculturally acceptable diluent or carrier.

Still further the invention provides a method of treating a fungal infection or leishmaniasis in an animal in need of such treatment which comprises administering to said animal an antifungal or antileishmanial effective amount of a compound of formula (I) or a pharmaceutically acceptable salt thereof.

Yet further, the invention provides a method of treating a fungal infection in a plant or seed in need of such treatment by contacting said plant or seed, or the locus of said plant, with an antifungal effective amount of a compound or agriculturally acceptable salt of formula (I).

Particularly preferred values for R are $CF_2CF_3$, $(CF_2)_2CF_3$ and $(CF_2)_3CF_3$. Particularly preferred as $R^1$ is hydrogen for reasons of economy.

Especially preferred invention compounds are:

2-(pentafluoroethyl)-1,3-bis-(1H-1,2,4-triazol-1-yl)propan-2-ol;

2-(heptafluoropropyl)-1,3-bis-(1H-1,2,4-triazol-1-yl)propan-2-ol;

2-(nonafluorobutyl)-1,3-bis-(1H-1,2,4-triazol-1-yl)propan-2-ol;

2-(heptafluoropropyl)-1,3-bis-(1H-1,2,4-triazol-1-yl)butan-2-ol; and 2-(nonafluorobutyl)-1,3-bis-(1H-1,2,4-triazol-1-yl)butan-2-ol.

Compounds in which $R^1$ is $CH_3$ exist as pairs of diastereoisomers, and the invention includes both the separated and unseparated pairs. Separation of the pairs can be carried out by well known methods, e.g. by column chromatography on silica gel.

An additional asymmetric center may arise in certain invention compounds wherein R is a branched $C_4$- or $C_5$-perfluoroalkyl group, and each of the possible isomers and their mixtures are included within the scope of this invention.

DETAILED DESCRIPTION OF THE INVENTION

The compounds of the formula (I) are prepared, for example, as outlined below.

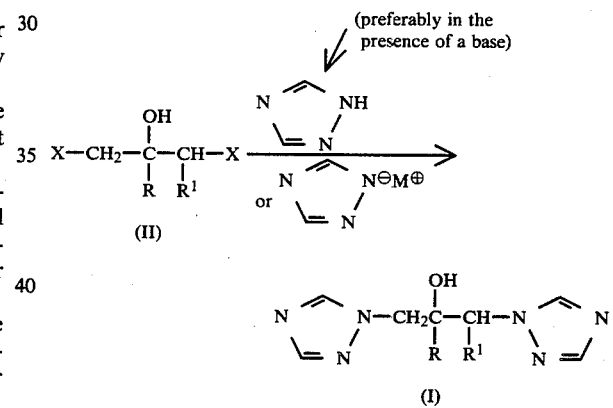

where X is a leaving group, for example, Cl, Br, I, $CH_3SO_2O-$, $CF_3SO_2O-$ or p-toluenesulphonyloxy and M is a cation, preferably Na, K or Li.

Preferably, X is Cl or Br.

The reaction is preferably carried out using 1,2,4-triazole in the presence of a base such as potassium carbonate, or by using an alkali metal salt of the triazole, preparable conventionally, e.g. from the triazole and sodium hydride.

Typically the reaction is completed by heating the reactants together in a suitable organic solvent, e.g. dimethylformamide, at a temperature in the range of 50°–130° C. until the reaction is complete, ordinarily in 2–24 hours. The product (I) is then isolated and purified by conventional methods, e.g. the solvent is evaporated, the residue taken up in a water immiscible solvent, washed with water and the solvent evaporated to afford the product of formula (I). This can be further purified, if desired, e.g., by column chromatography.

The starting materials of formula (II) are available by conventional synthetic methods, for example,

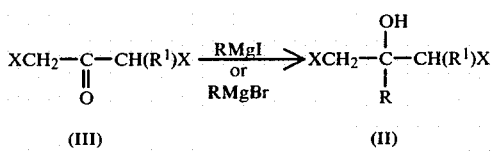

(III) (II)

Typically, the Grignard reagent is prepared at a sub-zero temperature in a dry ether solvent by contacting the perfluoroalkyl iodide (or bromide) with a molar excess of a lower molecular weight, commercially available Grignard reagent, e.g. phenylmagnesium bromide. A molar excess of the 1,3-dihaloketone (III) is added and the resulting mixture stirred at low temperature, preferably −50° to −20° C. until the reaction is substantially completed. The reaction is then quenched by addition of water or acetic acid and the desired product (II) isolated by extraction.

The 1,3-dihaloketones of formula (III) are commercially available compounds.

In the case where R is $CF_3$, the intermediate (II) is preferably prepared using the organozinc or organocopper derivative of trifluoromethyl iodide rather than the Grignard, as suggested in Chem. Letters, 1679 (1981) and ibid., 1453 (1982).

Pharmaceutically and agriculturally acceptable acid addition salts of the compounds of the formula (I) are those formed from strong acids which form non-toxic acid addition salts, such as hydrochloric, hydrobromic, sulphuric, oxalic and methanesulphonic acids.

The salts are obtained by conventional procedures, e.g. by mixing solutions containing equimolar amounts of the free base and desired acid, and the required salt is collected by filtration, if insoluble, or by evaporation of the solvent.

The compounds of the formula (I) and their pharmaceutically acceptable salts are antifungal agents, useful in combatting fungal infections in animals, including humans. For example they are useful in treating topical fungal infections in man caused by, among other organisms, species of Candida, Trichophyton, Microsporum or Epidermophyton, or in mucosal infections caused by Candida albicans (e.g. thrush and vaginal candidiasis). They may also be used in the treatment of systemic fungal infections caused by, for example, Candida albicans, Cryptococcus neoformans, Aspergillus fumigatus, Coccidioides, Paracoccidioides, Histoplasma or Blastomyces.

The in vitro evaluation of the antifungal activity of the compounds can be performed by determining the minimum inhibitory concentration (m.i.c.) which is the concentration of the test compound in a suitable medium at which growth of the particular microorganism fails to occur. In practice, a series of agar plates, each having the test compound incorporated at a particular concentration is inoculated with a standard culture of, for example, Candida albicans and each plate is then incubated for 48 hours at 37° C. The plates are then examined for the presence or absence of growth of the fungus and the appropriate m.i.c. value is noted. Other microorganisms used in such tests can include Cryptococcus neoformans, Aspergillus fumigatus, Trichophyton spp, Microsporum spp, Epidermophyton floccosum, Coccidioides immitis and Torulopsis glabrata.

The in vivo evaluation of the compounds can be carried out at a series of dose levels by intraperitoneal or intravenous injection or by oral administration, to mice which are inoculated with a strain of Candida albicans. Activity is based on the survival of a treated group of mice after the death of an untreated group of mice following 48 hours observation. The dose level at which the compound provides 50% protection against the lethal effect of the infection, the $PD_{50}$ in mg/kg, is noted.

Using the above test method, the following $PD_{50}$ values (mg/kg) were obtained with selected compounds of the invention in mice infected with Candida albicans:

| Compound of Example No. | Oral $PD_{50}$ (mg/kg) |
|---|---|
| 1 | 0.1 |
| 2 | 0.2 |
| 3 | 2.2 |
| 4 (pure diastereomer 1) | 0.1 |
| 4 (1:4 mixture of diastereomers 1 and 2) | 0.1 |
| 4 (pure diastereomer 2) | 0.1 |
| 5 (pure diastereomer 1) | 3.1 |
| 5 (3:2 mixture of diastereomers 1 and 2) | 0.7 |

Leishmaniasis is an infection caused by a parasitic flagellate protozoa of the genus Leishmania. It usually affects the skin, nasal cavities and pharynx, one form causing oriental boils, another kala azar or black fever.

The compounds of the formula (I) also have efficacy against both visceral leishmaniasis (L. donovani) and mucocutaneous leishmaniasis (L. tropica major strain L561). In mice, a 50% reduction in parasite number (L. donovani) and a 50% reduction in lesion size (L. tropica major) was found when the product of Example 1 was administered at a dose level of 5×20 mg/kg by the oral route.

For human use, the antifungal compound of formula (I), or a pharmaceutically acceptable acid addition salt thereof, can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of the formula (I) can be administered in the form of a suppository or pessary, or they can be applied topically in the form of a lotion, solution, cream, ointment or dusting powder. For example, they can be incorporated into a cream consisting of an aqueous emulsion of polyethylene glycols or liquid paraffin; or they can be incorporated, at a concentration of from 1 to 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Microorganisms used in such tests include *Cochliobolus carbonum*, *Pyricularia oryzae*, *Glomerella cingulata*, *Penicillium digitatum*, *Botrytis cinerea* and *Rhizoctonia solani*.

For agricultural and horticultural purposes the compounds and their agriculturally acceptable acid addition salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil, or other growing medium, and they may be used not only to eradicate disease, but also prophylactically to protect the plants or seeds from attack.

The following Examples illustrate the invention. All temperatures are in °C. Ratios of solvent mixtures are by volume. Percentages are by weight unless otherwise noted.

EXAMPLE 1

2-(Heptafluoropropyl)-1,3-bis(1H-1,2,4-triazol-1-yl)propan-2-ol

Both parts (A) and (B) of this Example were carried out under nitrogen.

(A) Heptafluoropropyliodide (5 g, 6.9 mmole) was stirred at −78° C. in dry diethylether (20 ml). A solution of phenylmagnesium bromide in ethyl ether (10 ml of a 1.88 M solution) was added over a half-hour period. When this addition was complete, the reaction mixture was stirred at −20° C. for one hour. To this solution was added, at −78° C., 1,3-dichloroacetone (3.25 g, 25.6 mmole) in dry diethylether (20 ml) dropwise, keeping the temperature below −65° C. The mixture was then stirred four hours between −20° and −50° C. Glacial acetic acid (3 ml) in diethylether (5 ml) was added slowly followed by water (15 ml). The mixture was allowed to warm to 5° C. and then the phases were separated. The aqueous phase was washed with ether (2×25 ml). The ethereal extracts were combined, dried (MgSO₄) and evaporated to give crude 1,3-dichloro-2-(heptafluoropropyl)propan-2-ol, which was used directly in the next step.

(B) The crude propanol from Part (A) was combined with 1,2,4-triazole (6 g) and anhydrous potassium carbonate (18 g) in dry dimethylformamide (DMF) (60 ml) was heated at 80° C. overnight. The mixture was then cooled, the DMF was removed, and the residue was taken up in ethyl acetate (200 ml), washed with water (3×100 ml), dried over MgSO₄, and evaporated. The resulting residue was chromatographed by flash chromatography on silica (230–400 mesh), eluting with a mixture of ethyl acetate and methanol (95:5 by volume) and then with a mixture of ethyl acetate and methanol (90:10 by volume). Evaporation of the product-containing fractions gave, after recrystallization from methylene chloride/hexane, 226 mg of the pure title compound, m.p. 106°–108° C. Analysis %: Found: C, 33.4; H, 2.5; N, 23.3. Calculated for $C_{10}H_9N_6OF_7$: C, 33.1; H, 2.5; N, 23.2.

EXAMPLES 2 and 3

The following compounds were prepared similarly to the procedure of Example 1, parts (A) and (B) from appropriate starting materials:

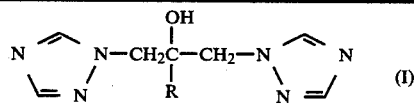

| Example No. | R | m.p. (°C.) | Analysis % (Theoretical in brackets) | | |
|---|---|---|---|---|---|
| | | | C | H | N |
| 2* | —(CF₂)₃CF₃ | 73–74 | 33.15 (33.1) | 2.5 2.5 | 19.3 19.7) |
| 3 | —CF₂CF₃ | 107–8 | 34.8 (34.6) | 2.9 2.9 | 27.1 26.9) |

*NMR analysis showed this product as being a solvate containing 2.1% ethyl acetate and 1.2% hexane.

In Example 3(A), 50% aqueous ammonium chloride was used in place of glacial acetic acid/diethylether/water.

EXAMPLE 4

2-(Heptafluoropropyl)-1,3-bis(1H-1,2,4-triazol-1-yl)butan-2-ol

Heptafluoropropyl iodide (15 g, 50.7 mmole) was stirred at −78° C. in dry diethyl ether (60 ml) and a solution of phenylmagnesium bromide (15 ml of a 3M solution) was added dropwise over 45 minutes. The mixture was stirred for a further 30 minutes after the addition was complete and a solution of 1,3-dibromobutan-2-one (9.3 g, 40 mmole) in dry diethylether (40 ml) was then added at such a rate that the temperature of the reaction mixture did not rise above −70° C. The mixture was stirred for a further 30 minutes at −70° C. after the addition was complete and was then allowed to warm to −40° C. over 30 minutes. The reaction mixture was kept at between −35° and −40° C. for 30 minutes and then at between −35° and −30° C. for a further 30 minutes. A solution of ammonium chloride (15 g) in water (170 ml) was then added and the mixture was allowed to warm to room temperature. The ether layer was separated and the aqueous layer was washed with ether (2×25 ml). The combined ether extracts were dried (MgSO4) and evaporated to give a pale yellow liquid (18 g) which was immediately added to a stirred mixture of 1,2,4-triazole (15 g, 0.22 mole) and anhydrous potassium carbonate (30 g) in dry dimethylformamide (70 ml). The mixture was stirred at 70° for three hours and then at room temperature overnight. The mixture was then poured into a mixture of water (300 ml) and ether (300 ml) and the ether layer was separated. The aqueous layer was washed with ether (2×300 ml) and the combined ether extracts were washed with water (3×100 ml), dried (MgSO4) and evaporated to give a pale yellow liquid (12 g, 77%) which was flash chromatographed on silica (230–400 mesh) eluting with ethyl acetate: methanol 95:5 by volume, to give *the title compound* as a diastereomeric mixture in the form of a pale yellow gum 2.8 g (18%). A 0.5 g sample of this gum was flash chromatographed again, using acetonitrile as the eluent, to give pure diastereoisomer 1 as a dihydrochloride salt after treatment with ethereal hydrogen chloride (0.11 g; hygroscopic white solid).

Analysis %: Found: C, 29.5; H, 2.9; N, 18.7. $C_{11}H_{11}F_7N_6O.2HCl$ requires: C, 29.4; H, 2.9; N, 18.7%.

Further elution gave, as a white solid, a 1:4 mixture of diastereoisomer 1 and diastereoisomer 2 as a dihydrochloride after treatment with ethereal hydrogen chloride, 0.09 g, m.p. 95°–98° C.

Analysis %: Found: C, 29.7; H, 2.9: N, 18.55. $C_{11}H_{11}F_7N_6O.2HCl$ requires: C, 29.4; H, 2.9; N, 18.7%.

A pure sample of diastereoisomer 2 was prepared by repeated preparative high pressure liquid chromatography on silica, eluting with a chloroform:acetonitrile mixture (1:1).

EXAMPLE 5

2-Nonafluorobutyl-1,3-bis(1H-1,2,4-triazol-1-yl)butan-2-ol

This compound was prepared by a procedure similar to that of Example 4 from the appropriate starting materials. However, in the final stage, the reaction mixture was heated at 50°–55° C. for 1.5 hours instead of at 70° C. for three hours. The title compound was again isolated as a diastereoisomeric mixture (2:1 ratio of diastereoisomers) (23% yield). A sample of this mixture was flash chromatographed on silica eluting with ethyl acetate:diethylamine (3:2 by volume) yielding pure diastereoisomer 1 as a dihydrochloride salt, m.p. 88°–94° C., after treatment with ethereal hydrogen chloride. The product was a hygroscopic white solid.

Analysis %: Found: C,28.1; H,2.5; N,17.0. Calculated for $C_{12}H_{11}F_9N_6O.2HCl$: C,28.9; H,2.6; N,16.8%.

Further elution gave a 3:2 mixture of diastereoisomers 1 and 2 as a gum, which after treatment with ethereal hydrogen chloride yielded the dihydrochloride salt as a white solid, m.p. 103°–8° C.

Analysis %: Found: C,29.1; H,2.3; N,17.0; . Calculated for $C_{12}H_{11}F_9N_6O.2HCl$: C,28.9; H,2.6; N,16.8%.

EXAMPLE 6

1,3-Dichloro-2-trifluoromethylpropan-2-ol

A mixture of commercial zinc powder (1.30 g, 0.02 mole), trifluoromethyl iodide (2.15 g, 11 mmole) and 1,3-dichloroacetone (5.6 g, 44 mmole) in 30 ml dimethylformamide (DMF) is irradiated in the water bath of an ultrasound laboratory cleaner (35 Watts, 32 KHz) for 30 minutes. The mixture is partitioned between 2% w/v aqueous hydrochloric acid and diethyl ether. The ether extract is dried (MgSO4) and the solvent evaporated to afford the title compound.

When 1,3-dibromobutan-2-one or 1,3-dichlorbutan-2-one is used in place of 1,3-dichloroacetone in the above procedure, the corresponding 1,3-dihalo-2-trifluoromethylpropan-2-ols are obtained.

EXAMPLE 7

By employing the appropriate perfluoralkyl iodide and 1,3-dihaloketone in the procedures of Part A of Examples 1 and 4 the following compounds of formula (II) are obtained in like manner.

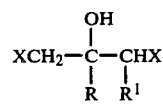

where X, R and $R^1$ are as defined below.

| X | R | $R^1$ |
|---|---|---|
| Cl | $CF_3(CF_2)_4$ | H |
| Cl | $CF_3$ | $CH_3$ |
| Br | $(CF_3)_2CF$ | H |
| Cl | $(CF_3)_2CFCF_2$ | H |
| Br | $(CF_3)_2CF(CF_2)_2$ | $CH_3$ |
| Cl | $(CF_3)_3C$ | H |

EXAMPLE 8

When the above 1,3-dihaloalkanols were reacted with 1,2,4-triazole by the procedures of Part B of Example 1 and 4, the corresponding products of the formula below were obtained where R and $R^1$ are as defined in Example 7.

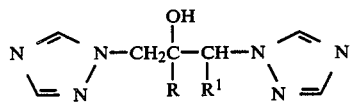

EXAMPLE 9

The following illustrate pharmaceutical compositions for the treatment of fungal infections:

(a) Capsule: 71 parts by weight of the compound of Example 1 are granulated with 3 parts maize starch and 22 parts lactose and then a further 3 parts maize starch and 1 part magnesium stearate are added. The mixture is regranulated and filled into hard gelatin capsules.

(b) Cream: 2 parts by weight of the compound of Example 4 (diastereomer 2) are dissolved in 10 parts of propylene glycol and mixed into 88 parts of a vanishing cream base.

(c) Pessary: 2 parts by weight of the compound of Example 3 are suspended in 98 parts of a warm liquified suppository base which is poured into moulds and allowed to solidify.

We claim:

1. A compound of the formula

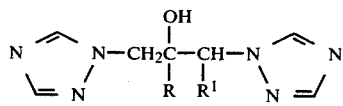

or a pharmaceutically or agriculturally acceptable acid addition salt thereof, wherein R is a $C_1$–$C_5$ perfluoroalkyl group; and $R^1$ is H or $CH_3$.

2. A compound according to claim 1, wherein R is —$CF_2CF_3$, —$(CF_2)_2CF_3$ or —$(CF_2)_3CF_3$.

3. A compound according to claim 2, wherein $R^1$ is H.

4. The compound according to claim 3: 2-(pentafluoroethyl)-1,3-bis-(1H-1,2,4-triazol-1-yl)propan-2-ol.

5. The compound according to claim 3: 2-(heptafluoropropyl)-1,3-bis-(1H-1,2,4-triazol-1-yl)propan-2-ol.

6. The compound according to claim 3: 2-(nonafluorobutyl)-1,3-bis-(1H-1,2,4-triazol-1-yl)propan-2-ol.

7. The compound according to claim 2: 2-(heptafluoropropyl)-1,3-bis-(1H-1,2,4-triazol-1-yl)butan-2-ol.

8. The compound according to claim 2: 2-(nonafluorobutyl)-1,3-bis-(1H-1,2,4-triazol-1-yl)butan-2-ol.

9. A pharmaceutical composition comprising an antifungal or antileishmanial amount of a compound or a pharmaceutically acceptable salt according to claim 1 and a pharmaceutically acceptable diluent.

10. An agricultural antifungal composition suitable for use on a plant or seed which comprises an antifungal amount of a compound or agriculturally acceptable salt according to claim 1 and an agriculturally acceptable diluent.

11. A method of treating a fungal infection or leishmaniasis in an animal in need of such treatment which comprises administering to said animal an antifungal or antileishmanial effective amount of a compound or pharmaceutically acceptable salt according to claim 1.

12. A method of treating a fungal infection in a plant or seed in need of such treatment which comprises contacting said plant or seed, or the locus of said plant, with an antifungal effective amount of a compound or agriculturally acceptable salt according to claim 1.

* * * * *